(12) United States Patent
Xiao et al.

(10) Patent No.: US 6,944,263 B2
(45) Date of Patent: Sep. 13, 2005

(54) APPARATUS AND METHODS FOR MULTIPLE VIEW ANGLE STEREOSCOPIC RADIOGRAPHY

(75) Inventors: Yongshun Xiao, Beijing (CN); Zhiqiang Chen, Beijing (CN); Li Zhang, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 73 days.

(21) Appl. No.: 10/743,277

(22) Filed: Dec. 22, 2003

(65) Prior Publication Data

US 2004/0208279 A1 Oct. 21, 2004

(51) Int. Cl.⁷ .............................................. A61B 6/02
(52) U.S. Cl. ...................................................... 378/41
(58) Field of Search .................................. 378/41, 42

(56) References Cited

U.S. PATENT DOCUMENTS 4,672,649 A * 6/1987 Rutt ............................ 378/10

* cited by examiner

Primary Examiner—Craig E. Church
Assistant Examiner—Jurie Yun
(74) Attorney, Agent, or Firm—Fredrikson & Byron, P.A.

(57) ABSTRACT

The multiple view angle X-ray stereoscopic imaging method of the present invention comprises the steps of: first, establishing the angle and distance indexes for all the pixel columns of a series of projected image data acquired along circular or spiral trace based on the X-ray imaging system parameters and data acquisition parameters, and sorting and storing the indexes so as to be retrieved fast; then, calculating the angle and distance parameters of pixels in the stereogram to be combined according to the selected observation viewpoint, direction of sight line, and parallax effect, and thereby looking up the stored indexes and the corresponding image data and implementing image combination. The method of the present invention provides a multiple view angle X-ray stereoscopic imaging display which can designate the position of viewpoint and direction of sight line, and adjust the parallax effect.

21 Claims, 3 Drawing Sheets

APPARATUS AND METHODS FOR MULTIPLE VIEW ANGLE STEREOSCOPIC RADIOGRAPHY

BACKGROUND OF THE INVENTION

1. Field of the Invention

The present invention relates to a field of radiographic digital image processing, and more particularly, to a multiple view angle X-ray stereoscopic imaging method and system thereof.

2. Description of the Related Art

X-ray imaging technology has been widely applied to various fields of industrial nondestructive testing, medical diagnosis, and scientific research. Three dimensional or stereoscopic display technology is used to enhance the spatial position information for radiography, and to enable examiners to understand better the spatial relations between defects or foreign matters. By capture a series of scanning images at different angles, Computerized Tomography (CT) calculates tomography images of an object using a tomography reconstruction algorithm, and renders a three dimensional image through a three dimensional visualization method. Although CT can obtain precise three dimensional spatial information, calculation amount of both reconstruction calculation and three dimensional rendering is very large and needs relatively long computation time such that it is difficult for CT to meet with the requirement for real-time application. Moreover, the price of whole system is also very expensive.

Since the stereoscopic X-ray imaging technology was presented in the initial stage of the twentieth century, most of the stereoscopic X-ray imaging systems have been designed by using the parallax principle. The principle of such a stereoscopic X-ray imaging system is described as follows. Two X-ray images corresponding to the left and right eyes are obtained by using various methods. Then the left eye sees only the image corresponding to the left eye and the right eye sees only the other image corresponding to the right eye using various display modes. Finally, the images corresponding to the left and right eyes are combined into a stereoscopic image by human brain. Stereoscopic images can enhance the spatial position information for images and improve the observation effects of the spatial structure relation of a examined object. A method most usually used for obtaining an X-ray stereogram is to shift the X-ray source or move an imaging screen between two exposures. Another method is to catch two images at different angles as an X-ray stereogram by rotating the X-ray source and imaging screen or rotating the object by a small angle. Although the methods for capture X-ray stereograms are different, all of them have such a defect that they only provide a stereoscopic image at the shooting angle, but the position of viewpoint, the direction of sight line, and the parallax are all fixed. Thus, these methods could not meet the parallax requirement for the human's observation. To obtain a stereoscopic image at other angles, shooting must be implemented again at another position.

SUMMARY OF THE INVENTION

In view of the problems and defects in the existing technologies, an object of the present invention is to provide a multiple view angle X-ray stereoscopic imaging method and system thereof. The method of the present invention provides a multiple view angle X-ray stereoscopic imaging display which can designate the position of viewpoint and direction of sight line, and adjust the parallax effect, thereby enabling examiners to implement interactive examination of stereoscopic X-ray images and to understand better the spatial structure of the examined object.

It is an object of the invention to provide a multiple view angle X-ray stereoscopic imaging method comprising the steps of:

1) obtaining the parameters of an imaging system by a method of measuring or calibrating;

2) projected image sampling: rotating a digital imaging acquisition device or an object placed in the same and making the digital imaging acquisition device and said object to generate relative circular movement or spiral movement, and acquiring a projected image $G_k(\theta)$ per $\theta$ degree, wherein $\theta$ is an any value;

3) establishing image indexes: compressing the acquired image data if required, storing the compressed data in the computer internal memory, and establishing two level sorted indexes for all image pixels based on the parameters of the imaging system;

4) setting viewpoint parameters: setting the viewpoint parameters of stereograms, by user, through an interactive interface according to the observation requirement in order to obtain stereograms having observation effects of different angles;

5) calculating sight line parameters: calculating the parameters of the corresponding sight line for each pixel in an image, said viewpoint parameters determine a current stereogram;

6) image indexes looking up: looking up the ray beams near to said sight line parameters in the image index table established in step 3), based on said sight line parameters calculated in step 5);

7) pixel combining: employing various filtering interpolation modes to implement the interpolation combination calculations for the near ray beams and combining an image pixel p'(i,j) corresponding to a sight line $L'_{ij}$, according to the operational performance of computers and the requirement of user for image precision, and achieving calculations for all pixels in stereograms by repeating steps 5) to 7);

8) image processing: implementing enhancement processing for images through an interactive interface according to the requirements of user;

9) stereoscopic displaying: realizing display of stereograms by a stereoscopic display device such that the left eye of the user can see only the image corresponding to the view angle of left eye and the right eye of the user can see only the other image corresponding to the view angle of right eye, and that thereby a stereoscopic image is formed.

It is another object of the invention to provide a multiple view angle X-ray stereoscopic imaging system comprising an X-ray imaging device formed of an X-ray source (1) and a flat plate X-ray detector (3), a table (2) which can rotate in multiple freedom, a scan control and data acquisition unit (4), a multiple freedom control unit (5), a stereoscopic display graphical card (7), an image analysis and processing unit (6), a display unit (8), and a pair of stereoscopic eyeglasses (9), wherein said X-ray digital imaging acquisition device is used for implementing a circular or spiral trace scanning;

said scan control and data acquisition unit is used for obtaining the parameters of an imaging system by a method of measuring or calibrating, and for rotating the digital imaging acquisition device or an object placed in the same and making the digital imaging acquisition device and said object to generate relative circular movement or spiral movement, and acquiring a projected image $G_K(\theta)$ per $\theta$ degree, wherein $\theta$ is any value;

said image analysis and processing unit (6) is used for establishing image indexes: compressing the acquired image data if required, storing the compressed data in the computer internal memory, and establishing two level sorted indexes for all image pixels based on the parameters of the imaging system; for setting viewpoint parameters: setting the viewpoint parameters of stereograms, by users, through an interactive interface according to the observation requirement in order to obtain stereograms having observation effects of different angles; for calculating sight line parameters: calculating the parameters of corresponding sight line for each pixel in images, wherein the viewpoint parameters determine a current stereogram; for image indexes looking up: looking up the ray beams near to said sight line parameters in said image index table, based on said sight line parameters calculated in step of calculating the parameters of sight line; for pixel combining: employing various filtering interpolation modes to implement the interpolation combination calculations for the near ray beams and combining an image pixel ($p'(i,j)$) corresponding to a sight line ($L'_{ij}$), according to the operational performance of computers and the requirement of user for image precision, and thereby achieving calculations for all pixels in stereograms; for image processing: implementing enhancement processing for images through an interactive interface according to the requirements of user; and for stereoscopic displaying: realizing display of stereograms by a stereoscopic display device such that the left eye of the user can see only the image corresponding to the view angle of left eye and the right eye of the user can see only the other image corresponding to the view angle of right eye, and that thereby a stereoscopic image is formed.

BRIEF DESCRIPTION OF THE DRAWINGS

The above and other objects, advantages, and features of the present invention will be more apparent from the following description taken in conjunction with the accompanying drawings in which.

DETAILED DESCRIPTION OF THE PREFERRED EMBODIMENTS

Best modes of carrying out the present invention will be described in further detail using various embodiments with reference to the accompanying drawings.

The multiple view angle X-ray stereoscopic imaging method of the present invention comprises the steps of: first, establishing the angle and distance indexes for all the pixel columns of a series of projected image data acquired along circular or spiral trace based on the X-ray imaging system parameters and data acquisition parameters, and sorting and storing the indexes so as to be retrieved fast; then, calculating the angle and distance parameters of pixels in the stereogram to be combined according to the selected observation viewpoint, direction of sight line, and parallax effect, and thereby retrieving the stored indexes and the corresponding image data and implementing image combination. A multiple view angle X-ray stereoscopic imaging system of the present invention comprises an X-ray digital imaging acquisition device having a function of realizing circular or spiral trace scanning, a known computer device, and a known stereoscopic display device. The X-ray digital imaging acquisition device inputs X-ray images into the known computer device. The known computer device above described combines the input X-ray images into stereoscopic images according to the multiple view angle stereoscopic imaging method of the present invention, and displays the stereoscopic images by the known stereoscopic display device. The structural feature of the known computer device exists in that it includes a scan control and data acquisition unit and an image analysis and processing unit.

Figure 1:
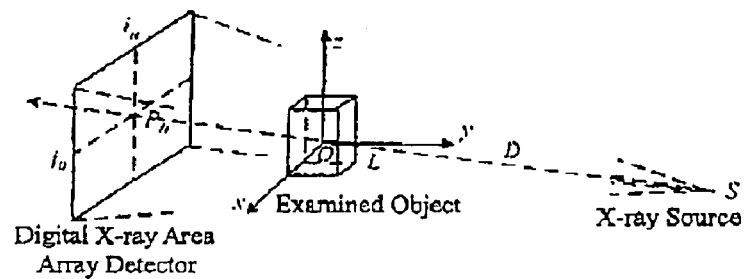
FIG. 1 is a schematic diagram showing an imaging process of the digital X-ray image acquisition apparatus in accordance with the present invention.

FIG. 1 shows a schematic diagram of imaging process of the X-ray digital imaging acquisition device according to the present invention. As shown in FIG. 1, an X-ray source is disposed at a point S and generates a cone beam. Generally, a radiographic radio source is one of X-ray source, accelerator and isotope source and the like according to different specific applications. A digital X-ray area array detector converts X-rays that transmit the examined object into photo signals by a scintillator crystal conversion screen or a fluorescent screen. Then the photo signals are subjected to photoelectric conversion and analog-digital conversion to obtain digital image data, which can be processed by a computer. Generally, a digital X-ray area array detector is an area array CCD detector or a digital flat plate detector and the like.

The examined object is disposed between the X-ray source and the area array flat plate detector. In the X-ray digital imaging acquisition device of the invention, the distance between the X-ray source and the area array detector is given as L, the distance between the X-ray source and the rotating center of the object is given as D and the spacing between pixels on the area array detector is given as $d_0$ (this parameter is determined by the producer of the area array detector). During the adjustment and calibration of imaging acquisition device, the X-ray source is adjusted such that X-ray perpendicular to the area array detector pass through the rotating axis of the examined object. Then the position of pixel $P_0(i_0,j_0)$ on the area array detector corresponding to the perpendicular X-ray is calibrated. The methods of calibration of the pixel $P_0(i_0,j_0)$ on the area array detector are depends on the parameters of the specific device. Usually, such a calibration is implemented by calculating the geometric relations between several images of a calibration object. More detail process of the calibration can be obtained from various existing technologies. During the acquisition process of imaging data, the distance L between the X-ray source and the area array detector, the distance D between the X-ray source and the rotating center of examined object, the spacing $d_0$ between pixels on the area array detector, and the pixel position $P_0(i_0,j_0)$ on the area array detector corresponding to the perpendicular X-ray have no change.

The operation flow of the scan control and data acquisition unit above described is as follows: 1) obtaining the parameters of an imaging system by a measuring or calibrating method; 2) rotating the digital imaging acquisition device or the object placed in the same and making the digital imaging acquisition device and said object to generate relative circular movement or spiral movement, and acquiring a series of projected image data per predetermined degree.

The operation flow of the image analysis and processing unit above described is as follows: 1) establishing image indexes, and calculating two level sorted index storage table; 2) viewpoint parameters setting; 3) sight line parameters calculating; 4) image index table looking up; 5) pixels interpolation combination; 6) image processing; and 7) stereoscopic displaying.

Figure 2:
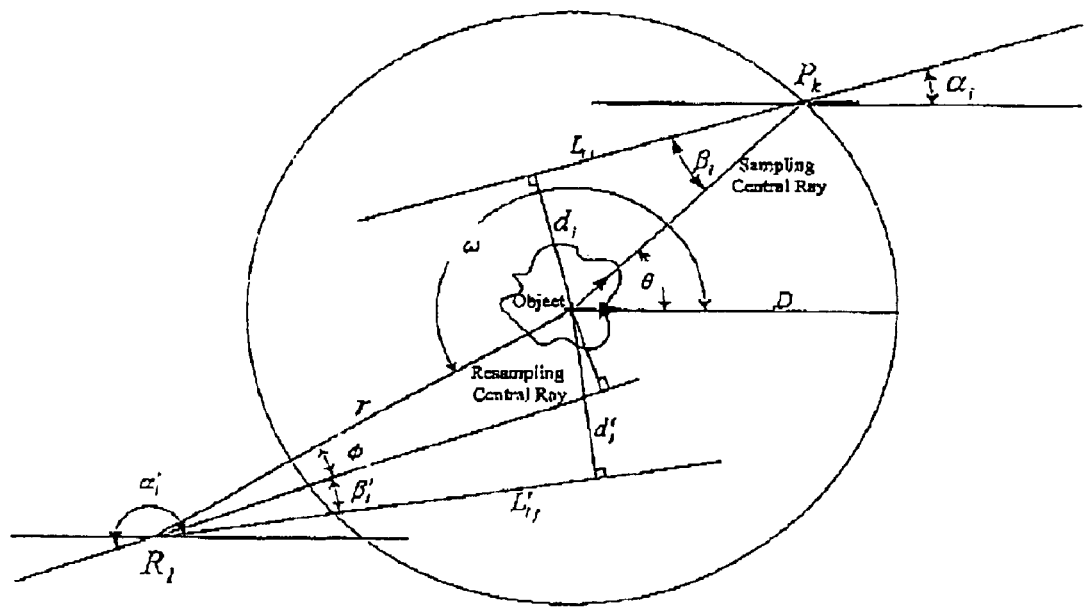
FIG. 2 is a geometrical schematic diagram showing calculations of sampled image data indexes and of image re-sampling in the method of multiple view angle X-ray stereogram combination according to the present invention.

With regard to the multiple view angle X-ray stereoscopic imaging method according to the present invention, the geometrical relation and the relevant parameters used in the image data acquisition sampling calculation and stereoscopic image combination resampling calculation are shown in FIG. 2. Since the loci of resampling viewpoint for the multiple X-ray stereoscopic image combination locate in a rotating plane where the X-ray source locates, FIG. 2 describes geometric relations formed by X-ray beam vertically projecting into the rotating plane for the sampling image and the resampling image. Thus, the angles shown in FIG. 2 are plane angles in the rotating plane.

In the multiple view angle X-ray stereoscopic imaging method of the invention, the image pixel index are established for the projected image sequence obtained by the scan control and data acquisition unit. Then, two level sorted index storage tables are calculated. In the FIG. 2, when rotating the object or imaging acquisition device and sampling k-th projected image with a rotation angle of θ, the following are defined. The location of the X-ray source is defined as a sampling viewpoint $P_k$, and the beam corresponding to pixel $P_0(i_0,j_0)$ of the projected image is defined as a sampling center ray, which pass through the center of the object and perpendicular to the area array detector. Further, the plane angle rotating from the reference coordinate axis in the rotating plane to the sampling center ray is defined as a rotation angle θ. The radius of the sampling circle shown in the FIG. 2 is the distance D between X-ray source and the rotating center of the object.

In the k-th projected image $G_k(\theta)$ sampled with the rotation angle θ, it is assumed that the X-ray beam corresponding to the pixel $P(i,j)$ is $L_{ij}$. Then, an image pixel index is established for the projected image $G_k(\theta)$. Namely, it is necessary to calculate the plane angle $\alpha_i$ of beam $L_{ij}$ corresponding to each pixel on the image $G_k(\theta)$ and the reference coordinate, and the horizontal distance $d_1$ from beam $L_{ij}$ to the rotation center axis of the object, as shown in FIG. 2.

In order to calculate parameters $\alpha_i$ and $d_i$, a horizontal angle $\beta_1$ in the rotation plane between beam $L_{ij}$ and the sampling center ray should be calculated firstly. Since the sampling center ray is perpendicular to the area array detector plane, two intersections of the sampling center ray and a line projected in the rotation plane by beam $L_{ij}$ and the area array detector, and the sampling viewpoint $P_k$ form three vertexes of a right-angled triangle. According to the geometric relations between sides and angles of a right-angled triangle, the length of a right-angled side against the angle $\beta_i$ is $(i-i_0) \times d_0$. And the length of the other side is the distance L from the X-ray source to the area array detector. Thus, the following is obtained:

$$\beta_i = \tan^{-1}\left[\frac{(i-i_0) \times d_0}{L}\right] \quad (1)$$

where $i_0$ is serial number of the pixel column corresponding to rotating central axis in the projected image, and $d_0$ is the spacing between detector pixels, and L is the distance from the X-ray source to the detector. The sign of $\beta_i$ denotes whether the ray $L_{i,j}$ lies in the left or right side of the sampling central ray. In the present embodiment, if $\beta_i<0$,$L_{ij}$ lies in the left of the sampling central ray; and if $\beta_i>0$,$L_{ij}$ lies in the right side of the sampling central ray.

Next, a line through the sampling viewpoint is made so that it is parallel to the reference coordinate. Then, an angle between the X-ray beam $L_{ij}$ and the parallel line is equal to $\alpha_i$. Accordingly, from the geometrical angle relation, the angle $\alpha_i$ is calculated in accordance with the angle $\beta_i$ and the rotation angle θ of the sampling viewpoint. In order to establish index table, the value range of the angle $\alpha_i$ of the X-ray $L_{i,j}$ is $[0,2\pi]$. From the relation between angles θ and $\beta_1$ the angle $\alpha_i$ is calculated using following equation:

$$\alpha_i = \begin{cases} \theta - \beta_i + 2\pi & (\beta_i > \theta) \\ \theta - \beta_i & (\beta_i < \theta < \beta_i + 2\pi) \\ \theta - \beta_i - 2\pi & (\theta > \beta_i + 2\pi) \end{cases} \quad (2)$$

The distance $d_i$ from the ray $L_{i,j}$ to the rotating central axis of the object is calculated by making a perpendicular line with respect to $L_{ij}$ through the rotation center. The perpendicular line, ray $L_{ij}$ and the sampling center ray form a right-angled triangle. According to geometric relations of triangle, the distance $d_1$ is calculated by using the following equation:

$$d_1 = D \times \sin(\beta_i) \quad (3)$$

wherein, D is the distance from the X-ray source to the rotation axis of the object, namely, the distance from the sampling viewpoint to the rotation axis of object, that is, hypotenuse of the triangle. Similar to $\beta_i$, the sign of $d_i$ denotes whether the ray $L_{i,j}$ lies in the left or right of the rotating central axis. If $d_i<0$,$L_{ij}$ lies in the left of the sampling central ray; and if $d_1>0$,$L_{ij}$ lies in the right side of the sampling central ray.

Figure 3:
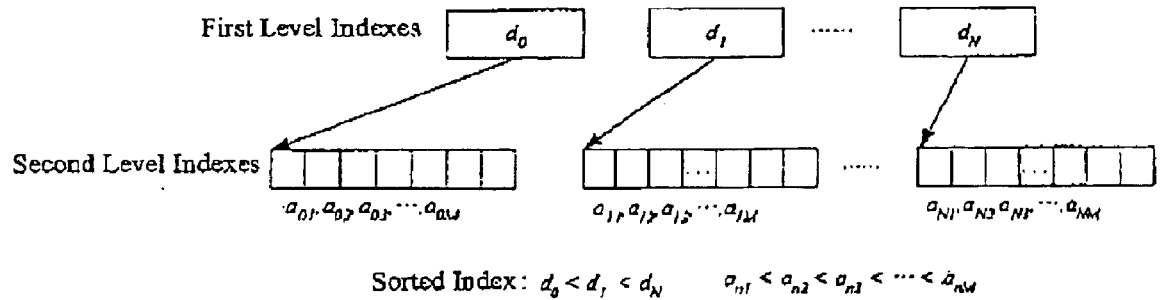
FIG. 3 is schematic diagram showing a storage mode of two level indexes of the sampled image data in the method of multiple view angle X-ray stereogram combination according to the present invention.

For each column of pixels in the sampled projected image, the projection angle $\alpha_1$ and central distance $d_i$ can index the corresponding ray beam. Considering the realization of looking up indexes fast in resampling, two level index looking up tables with priority to distance $d_i$ are established and stored in a structure as shown in FIG. 3. The distance $d_i$ from the ray beam to the rotating central axis, the serial number of the pixel column, and the index pointer of the projection angle are stored in the first level indexes. Then, the projection angle $\alpha_i$ having the same distance $d_i$ and the serial number of the projected image are stored in the second level indexes. The first level indexes are sorted by the distance $d_1$ and the second level is indexes are sorted by the projection angle $\alpha_1$ so as to employ the dichotomy method for looking up fast to improve the efficiency of image combination when resampling.

When an observation viewpoint, a direction of sight line, and a parallax are designated, the respective viewpoint and direction of sight line of the left and right images of a stereogram are calculated according to geometric relations in stereoscopic imaging method (see various of existing documents). For all pixels in the left and right images, the angle $\alpha'_i$ between the corresponding ray beam $L'_{ij}$ and the reference coordinate axis and the distance $d'_i$ from the ray beam $L'_{ij}$ to the rotating central axis of the object are solved. And the sampled ray beams having the values nearest to $\alpha'_i$ and $d'_i$ are selected to combine into a pixel corresponding to the ray $L'_{ij}$ by interpolation. FIG. 2 shows geometric relations used to implement resampling combination calculation at a resampling viewpoint $R_1$ when combining stereoscopic image. When calculating stereogram, the same calculation is performed for the left and right eyes' viewpoint. The resampling viewpoint $R_1$ for the image combination locates at the rotation plane where the sampling viewpoint locates. The viewpoint $R_1$ is denoted by the bearing angle $\omega$ between the viewpoint and the reference coordinate axis and the distance $\tau$ from the viewpoint to the rotating central axis of the original object. The direction of sight line is denoted by the resampling central ray which deviates by angle $\phi$ from the line connecting the viewpoint and the rotating axis of the object.

Similarly, first, the angle $\beta'_i$ between the ray beam $L'_{ij}$ and the center of resampling sight lines may be calculated based on the parameters of the imaging system. According to equation (1), the following equation is obtained:

$$\beta'_i = \tan^{-1}\left[\frac{(i-i_0) \times d_0}{L}\right] \quad (4)$$

Here, the sign of $\beta'_i$ denotes whether the ray $L_{i,j}$ lies in the left or right side of the sampling central ray. In the present embodiment, if $\beta'_i<0, L_{ij}'$ lies in the left of the sampling central ray; and if $\beta'_1>0, L_{ij}'$ lies in the right side of the sampling central ray. It is assumed that the field of view of resampling is the same as that of sampling.

The angle $\alpha'_i$ between the ray beam $L'_{ij}$ and the reference coordinate axis is calculated by using the following equation:

$$\alpha'_1 = \omega - (\phi + \beta'_i) \quad (5)$$

Wherein, $\omega$ is the bearing angle of viewpoint, and $\alpha'_1$ is normalized into the value range $[0, 2\pi]$ according to the result of calculation.

Similar to equation (3), the distance $d'_i$ from the ray beam $L'_{ij}$ to the rotating central axis of the object is calculated by using the following equation:

$$d'_i = r \times \sin(\phi + \beta'_i) \quad (6)$$

After obtaining the projection angle $\alpha'_1$ and distance $d'_i$ parameters of the ray beam $L'_{1j}$ to be combined, it is necessary to look up the rays having the values nearest to $\alpha'_i$ and $d'_1$ in the two level index table, and a suitable interpolation algorithm is selected to combine images according to the speed of image combination and requirement for image quality.

When stressing on the speed of image combination of algorithms, the nearest interpolation algorithm may be selected, in which it is necessary only to find a column of image data having the values nearest to $d'_i$ and $\alpha'_i$ in the two level index table in turn so as to implement pixel combination.

When stressing on the image quality of algorithms, the bilinear interpolation algorithm may be used so as to achieve a more precise image. First, two pointers nearest to the distance parameter $d'_1$ in the second level index table are looked up in the first level looking up table using a dichotomy method, and the distance parameters corresponding to the two indexes are labeled as $d_1$ and $d_2$ ($d'_1<d_i<d_2$).

Then, two indexes nearest to the projection angle parameters are looked up in the two second level index tables, and the projection angle parameters corresponding to four indexes are labeled as $\alpha_{11}$, $\alpha_{12}$ and $\alpha_{21}$, $\alpha_{21}$, assuming $\alpha_{11}<\alpha'_1<\alpha_{12}$ and $\alpha_{21}<\alpha'_i<\alpha_{22}$. Four columns of nearest pixels $P_{11}$, $P_{12}$, $P_{21}$, and $P_{22}$ obtained by indexing are combined with weight factors $r_1$, $r_2$, $r_3$, and $r_4$ respectively by interpolation:

$$P_{ij} = r_1 P_{11} + r_2 P_{12} + r_3 P_{21} + r_4 P_{22} \quad (7)$$

wherein, the weight factors $r_1$, $r_2$, $r_3$, and $r_4$ are calculated by using the following equations:

$$r_1 = \frac{d_2 - d'_i}{d_2 - d_1} \cdot \frac{\alpha_{12} - \alpha'_i}{\alpha_{12} - \alpha_{11}}, \quad r_2 = \frac{d_2 - d'_i}{d_2 - d_1} \cdot \frac{\alpha'_i - \alpha_{11}}{\alpha_{12} - \alpha_{11}}$$

$$r_3 = \frac{d'_i - d_1}{d_2 - d_1} \cdot \frac{\alpha_{22} - \alpha'_i}{\alpha_{22} - \alpha_{21}}, \quad r_4 = \frac{d'_i - d_1}{d_2 - d_1} \cdot \frac{\alpha'_i - \alpha_{21}}{\alpha_{22} - \alpha_{21}}$$

Due to deficiency in the parallax in the altitude direction for the stereograms combined on the basis of circular sampling, the parallax in the altitude direction may be achieved by interpolation directly with the same column of combined pixels in the altitude direction so as to keep the aspect ratio of the combined image. Assuming that the depth of sight line is the distance D from the rotating center of the object to the source, the image row number j corresponding to the j' in the sight line $L'_{ij}$ is calculated by using the following equation:

$$j = \frac{(j' - j_0) \times r}{D} + j_0 \quad (8)$$

wherein, $j_0$ is the serial number of a pixel row corresponding to the horizontal ray beam. Generally, the j row pixel in the combined pixel column is selected as the j' row pixel of the final combined image.

Figure 4:
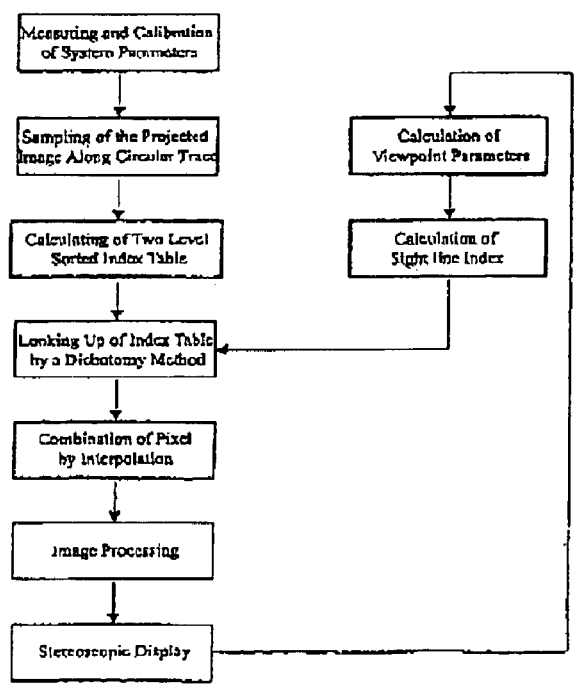
FIG. 4 is a flowchart showing operations of an image analysis and processing unit of the present invention.

FIG. 4 is a flowchart showing the multiple view angle X-ray stereoscopic imaging method of the invention. In the flowchart shown in FIG. 4, each of technical processing steps is specifically described as follows:

1) system parameters measuring and calibrating: obtaining the parameters L, D, $P_0(i_0,j_0)$ and $d_0$ of an imaging system by a method of measuring or calibrating.

2) projected image sampling along spiral or circular trace: rotating the digital imaging acquisition device or the object placed in the same and making the digital imaging acquisition device and said object to generate relative circular movement or spiral movement, and acquiring a projected image $G_k(\theta)$ per $\theta$ degree, wherein $\theta$ is any value.

3) calculating a two level sorted index table: the acquired image data are loaded into the computer internal memory, and may be compressed as required. In the computer, the angle and distance indexes are established for all image pixels based on the parameters of the imaging system. The sampling point of the k-th projected image is located at $P_k$, and its rotation angle $\theta$ is the angle between a sampling central ray (i.e., a ray corresponding to the rotating central axis of an object) and a reference coordinate axis located in the rotating plane. D is the radius of sampling circle. A ray beam corresponding to a pixel p(i,j) in the projected image $G_k(\theta)$ is denoted as $L_{ij}$. An angle $\beta_1$ between the $L_{ij}$ and the sampling central ray, an angle $\alpha_i$ between the $L_{ij}$ and the benchmark coordinate axis, and a distance $d_1$ from the $L_{ij}$ to the rotating center of an object can be calculated based on the parameters of the imaging system. The $\alpha_i$ and $d_1$ corresponding to each column of each image are stored in the two level sorting index tables.

4) viewpoint parameters setting: users set the viewpoint parameters of stereograms through an interactive interface according to the observation requirement in order to obtain stereograms having observation effects of different angles. By interactive operations, user can set the parameters including the position of viewpoint, the direction of observation sight line, the body of visual scene, and the parallax parameters of stereoscopic display, etc.

5) sight line parameters calculating; a current stereogram is determined by viewpoint parameters, and corresponding sight line parameters are calculated for each pixel in images. A sight line corresponding to a pixel point p'(i,j) is denoted as $L'_{ij}$. An angle $\alpha'_1$ between the sight line $L'_{ij}$ and the reference coordinate axis and a distance $d'_i$ from the $L'_{ij}$ to the rotating center of an object are calculated, and the value of image line number j corresponding to the height of the sight line $L'_{ij}$ is calculated by using the distance from the rotating center of an object to the source. The stereogram corresponding to the left and right eyes may be calculated based on viewpoint parameters by using the same method, except that the two viewpoints depart a distance of $t_c$ in the direction perpendicular to the center of sight lines.

6) index table looking up: ray beams near to the parameters of a sight line $L'_{ij}$ are looked up in the image index table established in step 3), according to the angle $\alpha'_i$ between the sight line $L'_{ij}$ and the reference coordinate axis and the distance $d'_1$ from the sight line $L'_{ij}$ to the rotating center of the object calculated in step 5). The number and selecting mode of the near ray beams are related to the image pixel synthesis filtering method selected in step 7).

7) pixel interpolation combination: according to the operational performance of computers and the requirement of user for image precision, various filtering interpolation modes may be employed to implement the interpolation combination calculations for the near ray beams, and an image pixel p'(i,j) corresponding to the sight line $L'_{ij}$ is combined. The method usually used includes the nearest interpolation, bilinear interpolation, quadratic interpolation, etc. Calculations for all pixels in stereogram are achieved by repeating steps 5) to 7).

8) image processing: functions of image enhancement processing such as gray transformation, pseudo color, edge enhancement, etc, are provided through an interactive interface to enhance the effect of stereoscopic display, according to the requirements of users.

9) stereoscopic displaying: display of stereograms is such realized by a stereoscopic display device that the left eye of the user can see only the image corresponding to the view angle of left eye and the right eye of the user can see only the other image corresponding to the view angle of right eye, and thereby the images corresponding to the left and right eyes are combined into a stereoscopic image. Users can change the position of observation viewpoint, the direction of observation sight line, and the parallax continually to achieve the examination effect of multiple angle stereoscopic displaying by repeating step 3) to 9).

Figure 5:
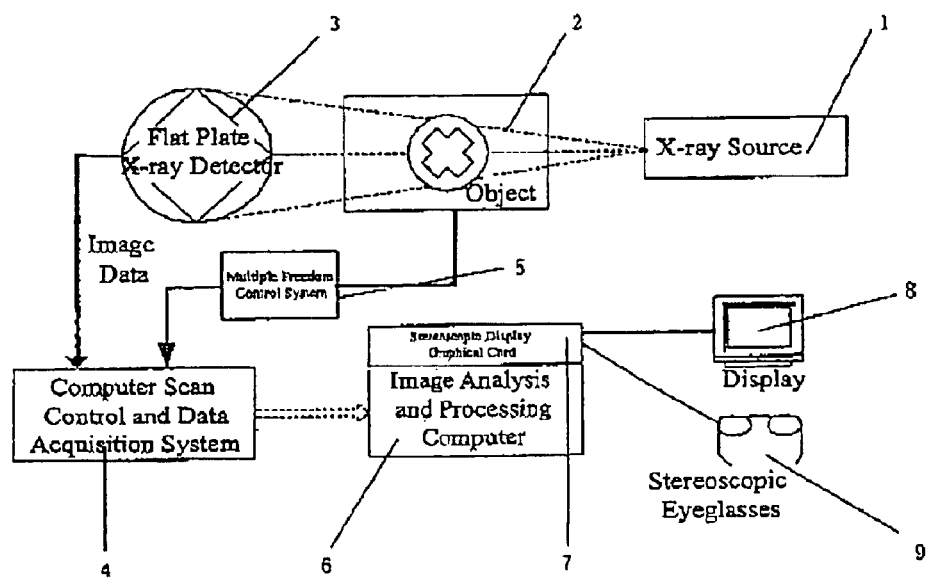
FIG. 5 is a block diagram showing a configuration of a preferred embodiment of the multiple view angle X-ray stereoscopic imaging system according to the present invention.

The multiple view angle X-ray stereoscopic imaging system described above is shown in FIG. 5. The multiple view angle X-ray stereoscopic imaging system of the invention comprises an X-ray imaging device formed of an X-ray source 1 and a flat plate X-ray detector 3, an table 2 which can rotate in multiple freedom, a scan control and data acquisition unit 4, a multiple freedom control unit 5, a stereoscopic display graphical card 7, an image analysis and processing unit 6, a display unit 8, and a pair of stereoscopic eyeglasses 9. The table 2 is located between the X-ray source 1 and the flat plate X-ray detector 3. The scan control and data acquisition unit 4 acquires the image data sent from the flat plate detector 3 by a data acquisition card, and acquires the scan position information about the table 2 sent from the multiple freedom control unit 5 by a communication port. The image analysis and processing unit 6 achieves image processing and combines stereoscopic images, based on the data sent from the scan control and data acquisition unit 4. The image analysis and processing unit 6 displays the stereograms inversely on the display unit 8 through the stereoscopic display graphical card 7, and drives the pair of stereoscopic eyeglasses 9. The scan control and data acquisition unit 4 and the image analysis and processing unit 6 may be mounted on the same PC, or may be also mounted on two different PCs connected via a network. The scan control and data acquisition unit 4 and the image analysis and processing unit 6 operate according to the multiple view angle X-ray stereoscopic imaging method.

With regard to the present invention, it is the known computer device that implements image processing and combines stereoscopic images based on the parameters of the imaging system and the projected image $G_k(\theta)$ acquired by the digital imaging acquisition device. Accordingly, the present invention provides a multiple view angle X-ray stereoscopic imaging display which can designate the position of viewpoint and direction of sight line and adjust the parallax effect, thereby enabling examiners to implement interactive examination of stereoscopic X-ray images and to understand better the spatial structure of the examined object. The present invention can realize fast stereoscopic image combination on advanced computers, and change view angle smoothly to observe variation of stereoscopic image, and enhance the stereoscopic effect caused by the motion parallax.

While the invention has been described in conjunction with the specific embodiments, it is apparent that the person skilled in the art could implement the invention by other modes, in addition to the circular and spiral sampling method. The X-ray source, X-ray detector, table rotating in multiple freedom, stereoscopic display device, and known computer device in the system of the present invention may be formed by devices of any number or specification. Accordingly, the scope of the present invention and claims is not limited to specific implementation system.

What is claimed is:

1. A multiple view angle X-ray stereoscopic imaging method comprising the steps of:
   1) obtaining the parameters of an imaging system by a method of measuring or calibrating;
   2) projected image sampling: rotating a digital imaging acquisition device or an object placed in the same and making the digital imaging acquisition device and said object to generate relative circular movement or spiral movement, and acquiring a projected image $G_k(\theta)$ per $\theta$ degree, wherein $\theta$ is any value;
   3) establishing image indexes: establishing two level sorted indexes for all image pixels based on the parameters of the imaging system;
   4) setting viewpoint parameters: setting the viewpoint parameters of stereograms, by user, through an interactive interface according to the observation requirement in order to obtain stereograms having observation effects of different angles;
   5) calculating sight line parameters: calculating the parameters of the corresponding sight line for each pixel in an image, said viewpoint parameters determine a current stereogram;

6) image indexes looking up: looking up the ray beams near to said sight line parameters in the image index table established in step 3), based on said sight line parameters calculated in step 5);

7) pixel combining: employing one or more various filtering interpolation methods to implement the interpolation combination calculations for the near ray beams and combining an image pixel (p'(i,j)) corresponding to a sight line ($L'_{ij}$), according to the operational performance of computers and the requirement of user for image precision, and achieving calculations for all pixels in stereograms by repeating steps 3) to 5);

8) image processing: implementing enhancement processing for images through an interactive interface according to the requirements of user;

9) stereoscopic displaying: realizing display of stereograms by a stereoscopic display device such that the left eye of the user can see only the image corresponding to the view angle of left eye and the right eye of the user can see only the other image corresponding to the view angle of right eye, and that thereby a stereoscopic image is formed.

2. The stereoscopic imaging method according to claim 1, wherein said two level indexes in step 3) are angle index and distance index.

3. The stereoscopic imaging method according to claim 2, wherein step 3) further comprising:

calculating a two level sorted index storage table.

4. The stereoscopic imaging method according to claim 3, wherein step 3) further comprising:

having the sampling point of the k-th projected image located at the sampling viewpoint ($P_k$) of the sampling circle, wherein the rotation angle ($\theta$) is the angle between a sampling central ray corresponding to the rotating central ray of an object and a reference coordinate axis located in the rotating plane, D is the radius of sampling circle, and a ray beam corresponding to a pixel p(i,j) in the projected image $G_k(\theta)$ is denoted as $L_{ij}$;

calculating the angle ($\beta_i$) between said ray beam ($L_{ij}$) and the sampling central ray, the angle ($\alpha_i$) between said ray beam ($L_{ij}$) and the reference coordinate axis, and the distance ($d_i$) from said ray beam ($L_{ij}$) to the rotating center of an object based on the parameters of the imaging system; and storing said angle ($\alpha_i$) and said distance ($d_i$) corresponding to each column of each image in said two level sorting index table to establish indexes.

5. The stereoscopic imaging method according to claim 1, wherein step 4) of setting viewpoint parameters comprising:

setting, by users, the parameters including the position of viewpoint, the direction of observation sight line, the body of visual scene, and the parallax parameters of stereoscopic display by interactive operations.

6. The stereoscopic imaging method according to claim 1, wherein step 5) of calculating sight line parameters comprising:

calculating the angle ($\alpha'_i$) between a sight line ($L'_{ij}$) corresponding to said pixel point (p'(i,j)) and a reference coordinate axis and the distance ($d'_i$) from said sight line ($L'_{ij}$) to the rotating center of an object;

calculating the value of image line number j corresponding to the height of said sight line ($L'_{ij}$) using the distance from the rotating center of an object to the source; and calculating the stereogram corresponding to the left and right eyes based on viewpoint parameters using the same method, wherein the two viewpoints depart a distance of ($t_c$) in the direction perpendicular to the center of sight lines.

7. The stereoscopic imaging method according to claim 1, wherein the number and selecting mode of the near ray beams in step 6) are related to the image pixel combination filtering method selected at step 7).

8. The stereoscopic imaging method according to claim 1, wherein the filtering interpolation method in step 7) includes at least one of the nearest interpolation, bilinear interpolation, and quadratic interpolation.

9. The stereoscopic imaging method according to claim 1, wherein said processing for image in step 8) includes at least one of gray transformation, pseudo color, and edge enhancement, to enhance the stereoscopic display.

10. The stereoscopic imaging method according to claim 1, wherein user can change the position of observation viewpoint, the direction of observation sight line, and the parallax continually to achieve the examination effect of multiple angle stereoscopic displaying, by repeating steps 2) to 7).

11. A multiple view angle X-ray stereoscopic imaging system comprising an X-ray imaging device formed of an X-ray source (1) and a flat plate X-ray detector (3), a table (2) which can rotate in multiple freedom, a scan control and data acquisition unit (4), a multiple freedom control unit (5), a stereoscopic display graphical card (7), an image analysis and processing unit (6), a display unit (8), and a pair of stereoscopic eyeglasses (9), wherein said X-ray imaging device is used for implementing a circular or spiral trace scanning;

said scan control and data acquisition unit is used for obtaining the parameters of an imaging system by a method of measuring or calibrating, and for rotating the digital imaging acquisition device or an object placed in the same and making the digital imaging acquisition device and said object to generate relative circular movement or spiral movement, and acquiring a projected image $G_k(\theta)$ per $\theta$ degree, wherein $\theta$ is any value;

said image analysis and processing unit (6) is used for establishing image indexes: establishing two level sorted indexes for all image pixels based on the parameters of the imaging system; for setting viewpoint parameters: setting the viewpoint parameters of stereograms, by users, through an interactive interface according to the observation requirement in order to obtain stereograms having observation effects of different angles; for calculating sight line parameters: calculating the parameters of corresponding sight line for each pixel in images, wherein the viewpoint parameters determine a current stereogram; for image indexes looking up: looking up the ray beams near to said sight line parameters in said image index table, based on said sight line parameters calculated in step of calculating the parameters of sight line; for pixel combining: employing one or more filtering interpolation methods to implement the interpolation combination calculations for the near ray beams and combining an image pixel (p'(i,j)) corresponding to a sight line ($L'_{ij}$), according to the operational performance of computers and the requirement of user for image precision, and thereby achieving calculations for all pixels in stereograms; for image processing: implementing enhancement processing for images through an interactive interface according to the requirements of user; and for stereoscopic displaying: realizing display of stereograms by a stereoscopic display device such that the left eye of the user can see only the image corresponding to the view angle of left eye and the right eye of the user can see only the other image corresponding to the view angle of right eye, and that thereby a stereoscopic image is formed.

12. The X-ray stereoscopic imaging system according to claim 11, wherein said table (2) is located between said X-ray source (1) and said flat plate X-ray detector (3), said scan control and data acquisition unit (4) acquires the image data sent from the flat plate detector (3) by a data acquisition card, and acquires the scan position information about the table (2) sent from the multiple freedom control unit 5 by a communication port, said image analysis and processing unit (6) achieves image processing and combines stereoscopic images, based on the data sent from the scan control and data acquisition unit (4), said image analysis and processing unit (6) displays the stereograms inversely on the display unit (8) through the stereoscopic display graphical card (7), and drives the pair of stereoscopic eyeglasses (9).

13. The X-ray stereoscopic imaging system according to claim 11, wherein the two level sorting indexes established by said image analysis and processing unit (6) based on the parameters of an imaging system are angle index and distance index.

14. The X-ray stereoscopic imaging system according to claim 12, wherein said image analysis and image processing unit (6) is further used for calculating a two level sorted index storage table.

15. The X-ray stereoscopic imaging system according to claim 13, wherein said image analysis and processing unit (6) makes the sampling point of the k-th projected image located at the sampling viewpoint ($P_k$) of the sampling circle, the rotation angle ($\theta$) of the k-th projected image is the angle between a sampling central ray corresponding to the rotating central ray of an object and a reference coordinate axis located in the rotating plane, D is the radius of sampling circle, a ray beam corresponding to a pixel (p(i,j)) in the projected image $G_k(\theta)$ is denoted as $L_{ij}$, an angle ($\beta_i$) between said ray beam ($L_{ij}$) and the sampling central ray, an angle ($\alpha_i$) between said ray beam ($L_{ij}$) and the reference coordinate axis, and a distance ($d_i$) from said ray beam ($L_{ij}$) to the rotating center of an object are calculated based on the parameters of the imaging system, and said angle ($\alpha_i$) and said distance ($d_i$) corresponding to each column of each image are stored in said two level sorting index table to establish indexes.

16. The X-ray stereoscopic imaging system according to claim 11, wherein said image analysis and processing unit (6), by interactive operations, enables user to set the parameters including the position of viewpoint, the direction of observation sight line, the body of visual scene, and the parallax parameters of stereoscopic display, etc.

17. The X-ray stereoscopic imaging system according to claim 11, wherein said image analysis and processing unit (6) calculates sight line parameters in the following manner:

calculating the angle ($\alpha'_i$) between a sight line ($L'_{ij}$) corresponding to said pixel point (p'(i,j)) and a reference coordinate axis and the distance ($d'_i$) from said sight line ($L'_{ij}$) to the rotating center of an object, and calculating the value of image line number j corresponding to the height of said sight line ($L'_{ij}$) using the distance from the rotating center of an object to the source; and calculating the stereogram corresponding to the left and right eyes based on viewpoint parameters using the same method, wherein the two viewpoints depart a distance of ($t_c$) in the direction perpendicular to the center of sight lines.

18. The X-ray stereoscopic imaging system according to claim 11, wherein the number and selecting mode of the near ray beams in said image analysis and processing unit (6) are related to the selected image pixel combination filtering method.

19. The X-ray stereoscopic imaging system according to claim 11, wherein said filtering interpolation method, implemented by said image analysis and processing unit (6), includes at least one of the nearest interpolation, bilinear interpolation, and quadratic interpolation.

20. The X-ray stereoscopic imaging system according to claim 11, wherein said image processing, implemented by said image analysis and processing unit (6), includes at least one of gray transformation, pseudo color, and edge enhancement, to enhance the stereoscopic display.

21. The X-ray stereoscopic imaging system according to claim 11, wherein said image analysis and processing unit (6) implements said projected image resampling, establishing image indexes, setting viewpoint parameters, image index looking up, and pixel combination repeatedly such that users can change the position of observation viewpoint, the direction of observation sight line, and the parallax continually to achieve the examination effect of multiple angle stereoscopic displaying.

* * * * *